(12) United States Patent  
Tsuji

(10) Patent No.: US 7,957,795 B2  
(45) Date of Patent: Jun. 7, 2011

(54) ABDOMINAL IMPEDANCE MEASUREMENT APPARATUS

(75) Inventor: Koji Tsuji, Niiza (JP)

(73) Assignee: Tanita Corporation, Tokyo (JP)

( * ) Notice: Subject to any disclaimer, the term of this patent is extended or adjusted under 35 U.S.C. 154(b) by 154 days.

(21) Appl. No.: 12/078,030

(22) Filed: Mar. 26, 2008

(65) Prior Publication Data

US 2008/0243026 A1 Oct. 2, 2008

(30) Foreign Application Priority Data

Mar. 27, 2007 (JP) ................. 2007-082538

(51) Int. Cl.  
*A61B 5/05* (2006.01)

(52) U.S. Cl. ..................................... 600/547

(58) Field of Classification Search .............. 600/547, 600/300, 372, 395; 29/825  
See application file for complete search history.

(56) References Cited

U.S. PATENT DOCUMENTS

| | | | | |
|---|---|---|---|---|
| 6,253,099 B1* | 6/2001 | Oskin et al. | ............. | 600/372 |
| 2005/0107719 A1* | 5/2005 | Arad (Abbound) | .......... | 600/547 |
| 2005/0222516 A1 | 10/2005 | Kasahara et al. | ............. | 600/547 |
| 2006/0282005 A1* | 12/2006 | Kasahara et al. | ............. | 600/547 |
| 2007/0038140 A1 | 2/2007 | Masuo et al. | | |

FOREIGN PATENT DOCUMENTS

| | | |
|---|---|---|
| JP | 11-113870 | 4/1999 |
| JP | 2001-145607 A | 5/2001 |
| JP | 2005-288023 | 10/2005 |
| JP | 2006-081601 A | 3/2006 |
| JP | 2007-014578 A | 1/2007 |
| JP | 2003-159227 A | 8/2008 |
| JP | 2008-237571 | 9/2008 |

OTHER PUBLICATIONS

Hermann Scharfetter et al., "Assessing Abdominal Fatness with Local Bioimpedance Analysis: Basics and Experimental Findings," [online], [Found in a search performed on Feb. 15, 2007], Internet URL: http://www.imt.tugraz.at/scharfetter/no_sync/publications/scharfetter_IJO_01.pdf#search='hermann%20scharfetter%20assessing%20abdominal.

Miwa Ryo, "Development of Visceral-fat Measuring Method Using Abdominal Bioelectrical Impedance," *Himan Kenkyu* (Journal of Japan Society for the Study of Obesity), Japan, Japan Society for the Study of Obesity, 2003, vol. 9, No. 2, pp. 32-38.

Chinese Office Action for Chinese Patent Application No. 200810082917.5.

* cited by examiner

*Primary Examiner* — Max Hindenburg  
*Assistant Examiner* — Brian Szmal  
(74) *Attorney, Agent, or Firm* — Hogan Lovells US LLP

(57) ABSTRACT

An abdominal impedance measurement apparatus includes a plurality of electrodes for measuring an abdominal impedance of a human subject, and includes an electrode supporting member for supporting the electrodes in such a manner that the electrodes protrude from the electrode supporting member. The electrode supporting member includes a plurality of segments aligned in a direction, the electrodes being respectively mounted on different segments, neighboring segments being connected rotatably with each other. The electrode supporting member further includes rotation-angle restricting parts for restricting relative rotation-angles between neighboring segments.

8 Claims, 4 Drawing Sheets

ABDOMINAL IMPEDANCE MEASUREMENT APPARATUS

BACKGROUND OF THE INVENTION

1. Field of the Invention

The present invention relates to abdominal impedance measurement apparatuses for human bodies.

2. Description of Related Art

In order for accurate measurements to be taken of areas of visceral fat and subcutaneous fat in the bodies of humans, body fat determination apparatuses have been used that calculate body fat data on the basis of tomographic images obtained by various CT (computed tomography) procedures, including X-ray CT and impedance CT, or by MRI (magnetic resonance imaging).

Conventionally, studies have been made in which indexes of body fat were calculated on the basis of impedances measured using impedance measuring electrodes that were brought into contact with the abdomen of a human subject. For example, according to one study, the mass or area of visceral fat of a human body is calculated on the basis of impedance measured using a pair of current-supplying electrodes in contact with the anterior and posterior surfaces of the abdomen and voltage-measurement electrodes in contact with the flanks of the abdomen, and on the basis of the waist circumference. The calculation method was obtained from correlations among the results of CTs, impedances, and the waist circumferences, as disclosed in *Development of Visceral-fat Measuring Method Using Abdominal Bioelectrical Impedance*, by Miwa RYO, Himan Kenkyu (Journal of Japan Society for the Study of Obesity), Japan, Japan Society for the Study of Obesity, 2003, Vol. 9, No. 2, pp. 32-38.

There has also been a study in which impedance measurement electrodes are mounted on a belt that is wound around the abdomen of a human subject, whereby the impedance measurement electrodes are brought into contact with the anterior surface of the abdomen, and the subcutaneous fat mass is estimated from the measured abdominal impedance, as disclosed in *Assessing abdominal fatness with local bio-impedance analysis: Basics and experimental findings*), by Hermann SCHARFETTER et al., (found in an online search on Feb. 15, 2007), URL: http://www.imt.tugraz.at/scharfetter/no_sync/publications/scharfetter_IJO_01.pdf#search='hermann%20scharfetter%20assessing%20abdominal' and in JP-A-11-113870.

In the measurement of bioimpedance in humans, even for one particular human subject, the measured results may vary depending on the positions of the measurement electrodes. Therefore, in order to ensure the reproducibility of measurements, the measurement electrodes should always be placed at the same locations. For example, it is possible to consider the transverse plane that passes through the navel of a human subject and is vertical to the median line to be the reference plane relative to which the measurement electrodes should always be arranged.

However, it is difficult, in practice, to arrange impedance measurement electrodes at such reference positions. For example, in the method in which a belt on which impedance measurement electrodes are arranged is wound around the abdomen, there is a possibility that the positions of the measurement electrodes may be out of alignment due to deformation of the belt. Furthermore, when the human subject is, for example, a bedridden disabled person or an elderly bedridden person, winding the belt around the abdomen requires a great deal of care.

JP-A-2005-288023 discloses, in FIG. 14, an apparatus for measuring impedance in which voltage-measurement electrodes are mounted on a fixed support and current-supplying electrodes are mounted on pivotable flaps. The electrodes are pressed onto the anterior surface of the abdomen of a human subject.

However, since the technique in JP-A-2005-288023 necessitates the pressing of the electrodes onto the anterior surface of the abdomen of a human subject, the measured results of impedance may vary depending on the strength of the pressing. The pivotable flaps on which the current-supplying electrodes are mounted are pivotable relative to the fixed support, but the pivot-angle of each flap with respect to the fixed support is manually adjusted and cannot be set constant even for a single human subject. The measured results of impedance may vary depending on the pivot-angle. Therefore, the same reproducibility of measurements is not always achieved.

SUMMARY OF THE INVENTION

Accordingly, the present invention provides an abdominal impedance measurement apparatus that enables the electrodes to be easily arranged at the abdomens of human subjects so that bioimpedance can be measured with a high degree of reproducibility.

According to the present invention, an abdominal impedance measurement apparatus includes: a plurality of electrodes for measuring an abdominal impedance of a human subject; and an electrode supporting member for supporting the electrodes in such a manner that the electrodes protrude from the electrode supporting member, the electrode supporting member including a plurality of segments aligned in a direction, each of the electrodes being mounted on a different segment, neighboring segments being connected rotatably with each other, the electrode supporting member including rotation-angle restricting parts for restricting relative rotation-angles between neighboring segments.

With such a structure, since the electrode supporting member includes segments connected mutually rotatably and each of the electrodes are mounted on different segments, by simply positioning the electrode supporting member, the electrode supporting member can be bent at the edges of segments around the outline of the abdomen of a human subject due to gravitational force exerted on the individual elements of the electrode supporting member, so that the electrodes protruding from the electrode supporting member are brought into contact with the abdomen of the human subject. Thus, the electrodes can be easily arranged at abdomens of human subjects. In addition, since the electrode supporting member can be bent and conforms to the outline of the abdomen of a human subject due to the gravitational force exerted on the individual elements of the electrode supporting member, whereby the electrodes are brought into contact with the abdomen of the human subject, no other force is necessary for maintaining the electrodes in contact with the abdomen of the human subject. Thus, for a particular human subject, each electrode comes in contact with the abdomen at a substantially constant force and at a substantially constant orientation (i.e., with a high level of reproducibility).

Furthermore, the rotation-angle restricting parts prevent mutual overrotation of segments. Since the cross section of the abdomen of a human subject is generally oval, it is preferable that the electrode supporting member be arranged around the abdomen of the human subject in such a manner that the electrode supporting member is bent at an obtuse angle, rather than at an acute angle, at the edges of the segments, so that each segment may be arranged substantially parallel to a part of the generally oval outline. Once the electrode supporting member is bent at a small angle, e.g., an acute angle, by mutual overrotation of segments, it takes some time to suitably arrange the electrode supporting member around the abdomen of the human subject. By virtue of preventing mutual overrotation of segments with the rotation-angle restricting parts, the time for suitably arranging the electrode supporting member around the abdomen of the human subject can be saved.

In a preferred embodiment, the plurality of electrodes includes two current-supplying electrodes for applying an electrical current to an abdomen of the human subject and two voltage-measurement electrodes brought into contact with two parts of the abdomen of the human subject for measuring a voltage between the parts with which the voltage-measurement electrodes are in contact. The current-supplying electrodes are mounted on two of the segments of the electrode supporting member. The voltage-measurement electrodes are mounted on two of the segments of the electrode supporting member that are different from the segments on which the current-supplying electrodes are mounted. At least one of the segments exists between the segment on which one of the current-supplying electrodes is mounted and the segment on which one of the voltage-measurement electrodes is mounted.

Since at least one of the segments exists between the segment on which one of the current-supplying electrodes is mounted and the segment on which one of the voltage-measurement electrodes is mounted, the degree of freedom of movement of the mechanism can be enhanced, and the length of the segments on which electrodes are mounted can be shortened, in comparison with a design in which the segment on which the current-supplying electrode is mounted is directly joined with the segment on which the voltage-measurement electrode is mounted. Thus, with respect to a plurality of human subjects of different body types, the electrode supporting member can be bent so as to conform to the various outlines of the abdomen, and with respect to a particular human subject, each electrode can be brought into contact with the abdomen at a substantially constant orientation.

In a preferred embodiment, the rotation-angle restricting parts of the electrode supporting member are provided such that the rotation-angle restricting parts located nearer a center of the electrode supporting member restrict a relative rotation-angle between neighboring segments within a larger range and such that the rotation-angle restricting parts located farther from the center of the electrode supporting member restrict a relative rotation-angle between neighboring segments within a smaller range. For common human body morphologies, such restrictions of rotation angles are preferable than a design in which the rotation-angle restricting parts located farther from the center of the electrode supporting member restrict a relative rotation-angle between neighboring segments within a larger range because such restrictions of rotation-angles facilitate the transformation of the electrode supporting member into a bent shape resembling the usual outline of the abdomen of a human subject, and the electrodes are arranged at appropriate positions with high reproducibility. Furthermore, the electrode supporting member can be promptly transformed from a straightly elongated condition into a bent shape resembling the outline of the abdomen of a human subject.

In a preferred embodiment, each of the electrodes includes a convex curved surface that may be brought into contact with the abdomen of the human subject, the convex curved surface being arranged apart from the electrode supporting member. A human subject with well-developed abdominal muscles, or a thin human subject, may have steep undulations on the anterior surface thereof due to the abdominal muscle. Therefore, if the electrodes do not include convex curved surfaces, there is a possibility that electrodes will not come into contact with the skin of the human subject even if the electrodes are faced toward the indentations of the abdominal muscle (positioned inside the indentations of the abdominal muscle). In contrast, when each of the electrodes includes a convex curved surface brought into contact with the abdomen of the human subject and the convex curved surfaces are arranged apart from the electrode supporting member, the electrodes securely come into contact with the skin of the human subject even if the electrodes are faced toward the indentations of the abdominal muscle (positioned inside the indentations of the abdominal muscle).

DETAILED DESCRIPTION OF PREFERRED EMBODIMENTS

Figure 1:
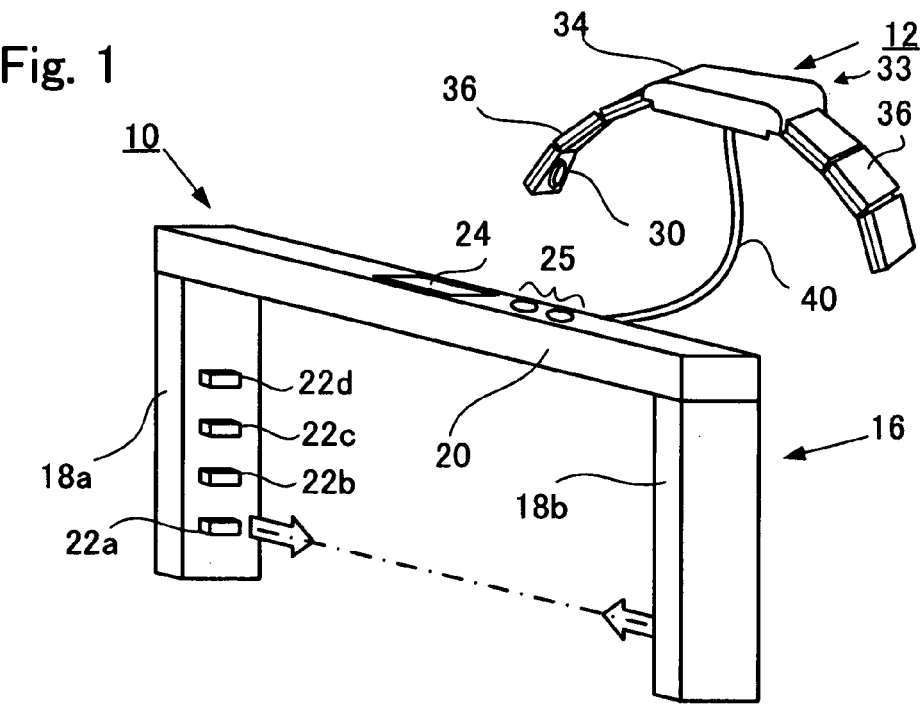
FIG. 1 is a perspective view showing a body composition determination apparatus according to an embodiment of the present invention.

With reference to the accompanying drawings, an embodiment according to the present invention will be described hereinafter. In the drawings, scales of lengths may differ from those in an actual product.

Figure 2:
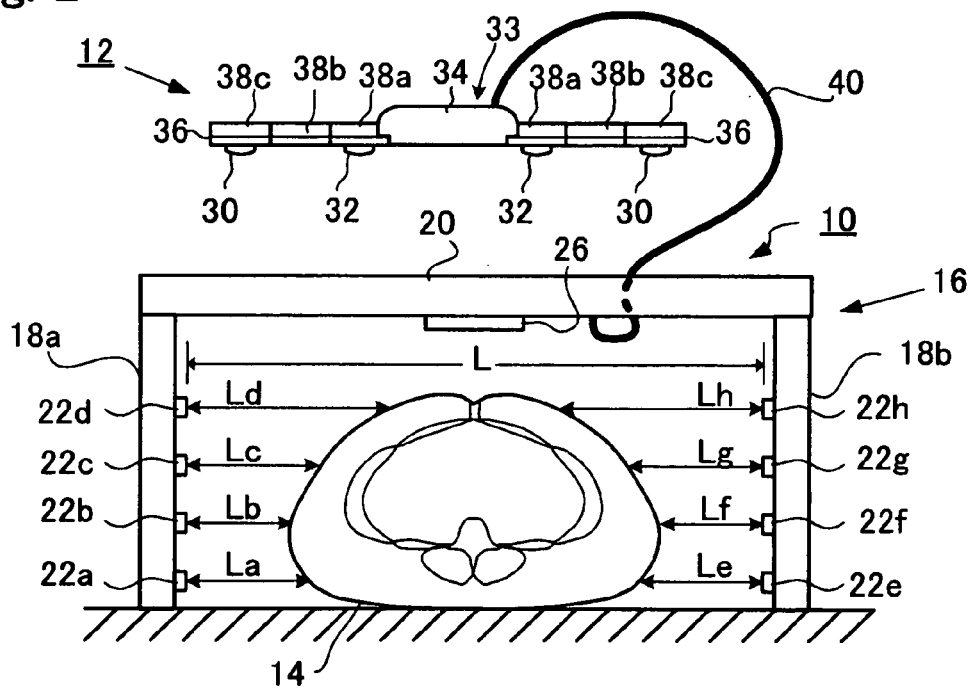
FIG. 2 is a front view showing the body composition determination apparatus in FIG. 1.

FIG. 1 is a perspective view of a body composition determination apparatus according to an embodiment of the present invention, and FIG. 2 is a front view of the body composition determination apparatus. The body composition determination apparatus includes an abdominal width determination apparatus 10 and an impedance measuring unit 12. As will be described later, the abdominal impedance measurement apparatus according to the embodiment includes some parts of the abdominal width determination apparatus 10 and the entirety of the impedance-measuring unit 12.

As shown in FIG. 2, the abdominal width determination apparatus 10 includes a casing (housing), i.e., a frame 16, in the inside of which a human being, i.e., a human subject 14, may be positioned. The frame 16 is portable, and it is generally U-shaped and generally rectangular and has one side that is open, whereby the human subject may be easily positioned inside the frame. Therefore, even if the human subject 14 is a bedridden disabled person or an elderly bedridden person, the frame 16 can be positioned easily around the human subject 14.

The frame 16 has a pair of generally parallel legs 18a and 18b and a connection part 20 fixed on the top of each of the legs 18a and 18b. The legs 18a and 18b are placed on a floor or bed on which the human subject 14 lies supine, and the connection part 20 is opposed to the anterior surface of the abdomen of the human subject 14, with the subject lying on the subject's back.

Distance measuring devices are mounted on the frame 16 for measuring distances among a plurality of known positions and a plurality of measured points on the outline of the human subject 14. In this embodiment, the distance measuring devices include a plurality of optical distance sensors 22 mounted on the inner surfaces of the frame 16. The optical distance sensors 22 are arranged in a perpendicular plane. In the drawings, the letters "a" through "h" are appended to reference number 22 in order to identify individual distance sensors 22. In the illustrated embodiment, eight distance sensors 22a through 22h are provided, but the number of distance sensors 22 is not limited to that in this embodiment. The sensors 22a through 22d are fixedly secured at the leg 18a, whereas the sensors 22e through 22h are fixedly secured at the leg 18b. The distance-interval between the array of the sensors 22a through 22d and the array of the sensors 22e through 22h is referred to as L.

Although it is not shown, each of the optical distance sensors 22 includes a light emitter for emitting a light beam (such as, for example, but not limited to, an infrared light beam) and a light receiving element for receiving the light reflected from a measured point on the human subject 14. On the basis of the state of the received light, the light receiving element generates an electrical signal corresponding to the distance from the corresponding sensor to the measurement point.

La through Lh in FIG. 2 designate the distance measured by the sensors 22a through 22h, respectively. The light receiving element of each optical distance sensor 22 receives light reflected from a point at which the horizontal line (distance-measurement line) passing through the corresponding distance sensor 22 intersects with the human subject 14. This point is the measurement point that the distance sensor 22 measures. For example, the light receiving element of the optical distance sensors 22a receives light reflected from a point at which the horizontal line passing through the corresponding distance sensor 22a intersects with the human subject 14, and it generates an electrical signal corresponding to the distance La from the corresponding sensor 22a to the point. Similarly, sensors 22b through 22h generate electrical signals corresponding to the distances Lb through Lh, respectively. The arrows in FIG. 1 represent directions of the distance-measurement lines of the sensors 22a and 22e. The dashed line connecting the sensors 22a and 22e indicates that the distance-measurement lines are in one straight line. The distance-measurement lines of the sensors 22b and 22f are also in a straight line. The distance-measurement lines of the sensors 22c and 22g are also in a straight line. The distance-measurement lines of the sensors 22d and 22h are also in a straight line.

A console of the body composition determination apparatus is disposed at the connection part 20. More specifically, as shown in FIG. 1, there are provided a display 24 for displaying operation guidance of the body composition determination apparatus and determination results, and a manual interface 25 including buttons, etc., for providing commands to the body composition determination apparatus in response to manipulation by the operator. Inside the connection part 20, electrical circuitry, which will be described later, is provided for controlling the body composition determination apparatus 1.

As shown in FIG. 2, a light emitter 26 is located at the connection part 20 for emitting a light beam toward the inside of the frame 16. The light emitter 26 may be, for example, but is not limited to, a laser that emits one or more light beams, in each of which the cross section is narrow. The light emitter 26 may be constituted of a plurality of light emitting elements that emit a plurality of light beams, respectively, or may be constituted of a single light emitting element.

By the aid of the light beams emitted from the light emitter 26, the operator can adjust the frame 16 (and thus the sensors 22a through 22h) to an appropriate position and an appropriate orientation with respect to the human subject 14. For example, the frame 16 can be deployed in the transverse plane that passes through the navel of the human subject 14 and is vertical to the median line of the human subject 14, and thereby, the sensors 22a through 22h may be deployed in the transverse plane. By the aid of the light beams emitted from the light emitter 26, the operator can also adjust the impedance measuring unit 12 to an appropriate position and an appropriate orientation with respect to the human subject 14. For example, the impedance measuring unit 12 can be located in the transverse plane that passes through the navel of the human subject 14 and is vertical to the median line of the human subject 14, whereby the electrodes 30 and 32 are also located in the transverse plane.

Figure 3:
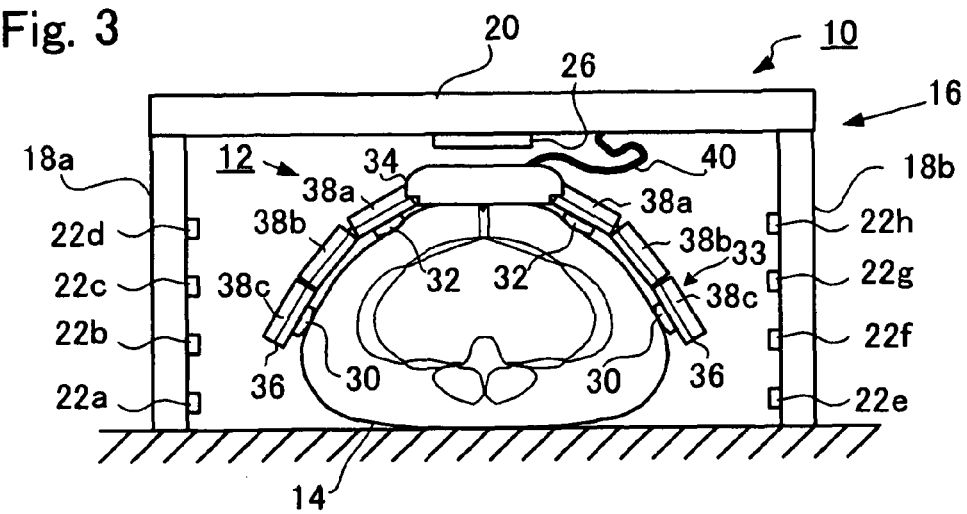
FIG. 3 is a front view showing the body composition determination apparatus in FIG. 1, which is measuring bioimpedance of a human subject.
Figure 4:
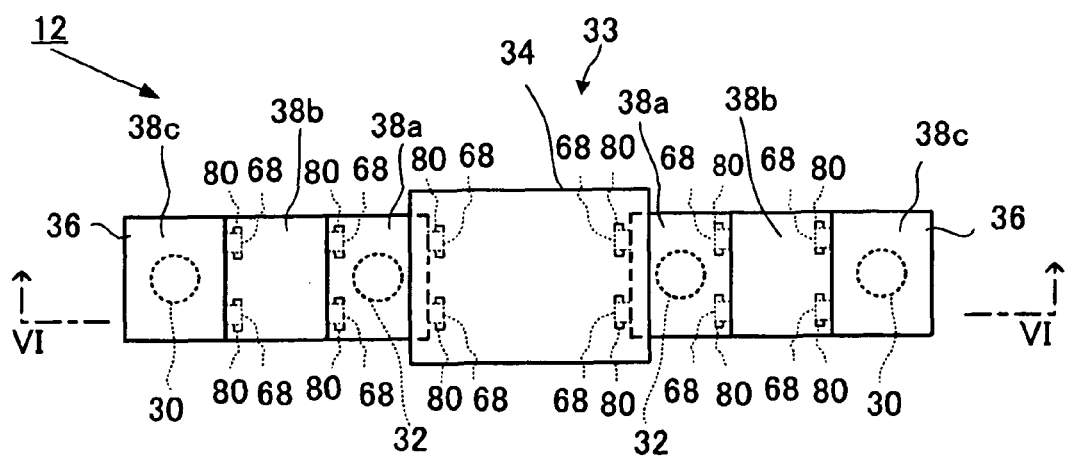
FIG. 4 is a plan view showing an impedance-measuring unit in the body composition determination apparatus in FIG. 1.

As shown in FIGS. 2 through 4, the impedance measuring unit 12 includes a plurality of electrodes 30 and 32 for measuring the abdominal impedance of a human subject, and an electrode supporting member 33 for supporting the electrodes 30 and 32. The electrode supporting member 33 includes a handle segment (central segment) 34 that the operator holds, and a pair of arms 36 extending from each end of the handle segment 34 in the longitudinal direction of the handle segment 34. In this embodiment, each arm 36 includes three arm segments 38a, 38b, and 38c, but the number of arm segments constituting each arm is not limited to that in this embodiment. As shown in FIG. 4, the segments (including the handle segment 34 and the arm segments 38a, 38b, and 38c) are aligned in a direction when viewed from the direction perpendicular to the sheet of FIG. 4.

As will be described in detail, the arm segment 38a is hinged to the handle segment 34, the arm segment 38b is hinged to the arm segment 38a, and the arm segment 38c is also hinged to the arm segment 38b. Therefore, the electrode supporting member 33 of the impedance measuring unit 12 can be bent at the edges of these elements. These arm segments are all of the same size, and the impedance measuring unit 12 is axisymmetric with respect to the handle segment 34 when both arms 36 are in mutually corresponding positions.

Electrodes 30 and 32 are respectively mounted on different segments. Current supplying electrodes 30 are attached to the lower surface of the arm segments 38c that are farthest from the handle segment 34, whereas voltage-measurement electrodes 32 are attached to the lower surface of the arm segments 38a that are nearest to the handle segment 34. Consequently, in each arm 36, one segment 38b is interposed between the segment 38c on which one of the current-supplying electrodes 30 is mounted and the segment 38a on which one of the voltage-measurement electrodes 32 is mounted. However, the number of arm segments between the current-supplying electrode 30 and the voltage-measurement electrode 32 in each arm is not limited to that in this embodiment, and the number may be two or more.

The electrodes 30 and 32 are supported by the arm segments in such a manner that the electrodes 30 and 32 protrude from the arm segments. The electrodes 30 and 32 are used in such a manner that they are in contact with the human subject 14 as shown in FIG. 3, that is, the current-supplying electrodes 30 apply an electrical current to the human subject 14 and the voltage-measurement electrodes 32 are used for measuring the voltage between the voltage-measurement electrodes 32. The bioimpedance of the abdomen of the human subject 14 can be calculated on the basis of the current and the voltage. Since the electrode supporting member 33 of the impedance measuring unit 12 is bendable, the electrodes 30 and 32 can be appropriately in contact with the abdomen of the human subject 14. As shown in FIG. 4, the electrodes 30 and 32 are aligned in the longitudinal direction of the electrode supporting member 33 when viewed from the direction perpendicular to the sheet of FIG. 4.

Inside the connection part 20 of the frame 16, a current-supply circuit 42 (see FIG. 5) is provided for supplying an electrical current to the current-supplying electrodes 30, and a voltage-measurement circuit 44 (see FIG. 5) is provided for measuring the voltage between the measurement electrodes 32. A cable 40 connecting the connection part 20 and the handle segment 34 contains wires for electrically connecting these circuits and the electrodes 30 and 32. The impedance measuring unit 12 is movable with respect to the frame 16 within a space defined by the length of the cable 40.

Figure 5:
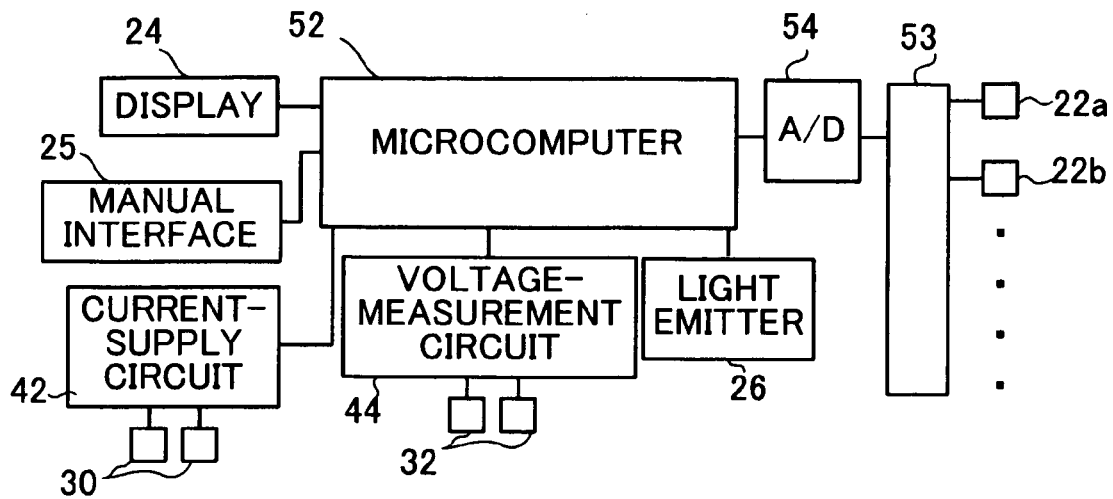
FIG. 5 is a block diagram showing an electrical structure of the body composition determination apparatus in FIG. 1.

Next, with reference to FIG. 5, the electrical structure of the body composition determination apparatus will be described. Inside the connection part 20 of the frame 16, electrical circuitry is provided for controlling the body composition determination apparatus 1. More specifically, inside the connection part 20, a microcomputer 52, a switch 53, an A/D (analog-to-digital) converter 54, the aforementioned current-supply circuit 42, and the aforementioned voltage-measurement circuit 44 are provided. The microcomputer 52 is electrically connected with the display 24, the manual interface 25, the current-supply circuit 42, the voltage-measurement circuit 44, the light emitter 26, and A/D converter 54.

In response to a command from the manual interface 25, the microcomputer 52 causes the light emitter 26 to emit light beams. In response to a command to determine the abdominal width from the manual interface 25, the microcomputer 52 drives a driving mechanism for the sensors (not shown) to cause the light emitting elements of the sensors 22$a$ through 22$h$ to emit the light beams.

The switch 53 transfers the output signals from the light receiving elements of the optical distance sensors 22$a$ through 22$h$ to the A/D converter 54 one by one in sequence. The A/D converter 54 converts the signal supplied from the switch 53 into a digital signal sequentially. The digital signal is supplied to the microcomputer 52. Thus, the digital distance signals corresponding to the output signals from the optical distance sensors 22$a$ through 22$h$ are supplied to the microcomputer 52. Each of the digital distance signals represents the gap distance between the corresponding optical distance sensor 22 and the measured point on the human subject 14 corresponding to the corresponding optical distance sensor 22.

The microcomputer 52 serves as a width estimator for estimating the abdominal width value of the human subject 14 on the basis of the distance signals output from the sensors. For this purpose, the microcomputer 52 calculates the between-measured-point distances of the abdomen of the human subject 14 on the basis of the distance signals. More specifically, based on the distance signals from the sensors 22$a$ and 22, the microcomputer 52 calculates between-measured-point distance W1 in accordance with the following equation (see FIG. 2):

$$W1 = L - La - Le$$

On the basis of the distance signals from the sensors 22$b$ and 22$f$, between-measured-point distance W2 is calculated as W2=L−Lb−Lf. Furthermore, based on the distance signals from the sensors 22$c$ and 22$g$, between-measured-point distance W3 is calculated as W3=L−Lc−Lg, whereas based on the distance signals from the sensors 22$d$ and 22$h$, between-measured-point distance W4 is calculated as W4=L−Ld−Lh.

Afterward, serving as the width estimator, the microcomputer 52 selects the maximum value from among between-measured-point distances W1 through W4. This maximum value is taken as the abdominal width value of the human subject 14. The microcomputer 52 causes the display 24 to show the width value.

Upon receiving a command to measure impedance from the manual interface 25, the microcomputer 52 drives the current-supply circuit 42 and the voltage-measurement circuit 44, so that the current-supply circuit 42 passes an electrical current between the current-supplying electrodes 30 and the voltage-measurement circuit 44 measures the voltage between the voltage-measurement electrodes 32. The microcomputer 52 calculates the bioimpedance that is related to the ratio of the voltage measured by the voltage-measurement circuit 44 to the current supplied to the current-supplying electrodes 30.

The abdominal impedance measurement apparatus according to the embodiment includes the aforementioned impedance measuring unit 12 and some parts (specifically, the frame 16, the light emitter 26, and the microcomputer 52) of the abdominal width determination apparatus 10.

The microcomputer 52 further serves as a body composition index calculator for calculating body composition indexes on the basis of the impedance measured by the abdominal impedance measurement apparatus (i.e., calculated by the microcomputer 52) and the width value estimated by the microcomputer 52. The body composition indexes include, for example, but are not limited to, subcutaneous fat thickness, abdominal muscle thickness, subcutaneous fat area, visceral fat area, total fat area of the abdomen, fat ratio of the torso, and fat ratio of the entire body. The theories for determining the body fat are known, e.g., in Japanese Patent Application Publication JP-2005-288023-A (published in 2005), and they are therefore not described here. The disclosure of Japanese Patent Application Publication JP-2005-288023-A is herein incorporated by reference in its entirety. The microcomputer 52 causes the display 24 to show these calculated indexes.

Figure 6:
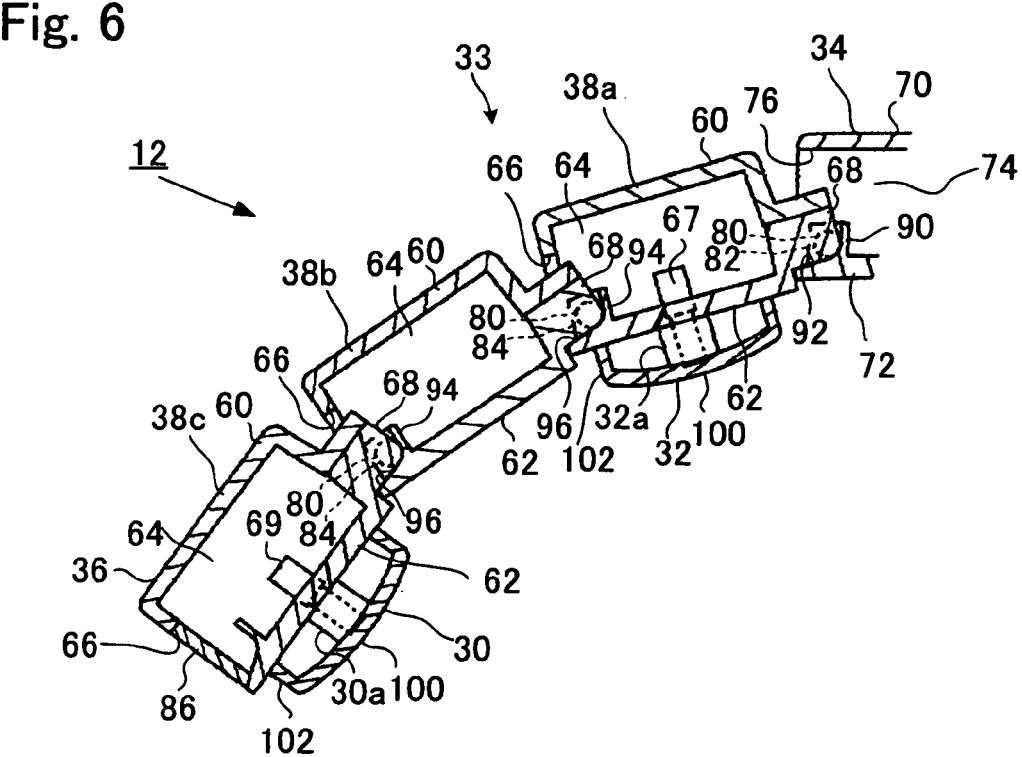
FIG. 6 is a cross sectional view taken along lines VI-VI in FIG. 4.

FIG. 6 is a cross sectional view taken along lines VI-VI in FIG. 4. In FIG. 6, one of the arms 36 is shown at a larger scale, but the other arm 36 is symmetric and similar to that shown in FIG. 6. With reference to FIG. 6, particulars of the segments of the electrode supporting member 33 (including the handle segment 34 and the arm segments 38$a$, 38$b$, and 38$c$) will be described.

As shown in FIG. 6, each of the arm segments 38$a$, 38$b$, and 38$c$ includes an upper casing 60 and a lower casing 62 fixed to each other and has a hollow structure with an internal space 64 defined by the casings 60 and 62. Similarly, the handle segment 34 includes an upper casing 70 and a lower casing 72 fixed to each other and has a hollow structure with an internal space 74 defined by the casings 70 and 72. In the internal space 64 of the arm segment 38a, a screw 67 made of an electrical conductor is arranged so as to penetrate the lower casing 62 of the arm segment 38a, and is secured to a hub 32a of one of the voltage-measurement electrodes 32 having a hollow structure. The voltage-measurement circuit 44 in FIG. 5 is connected with the screw 67 via a wire (not shown). On the other hand, in the internal space 64 of the arm segment 38c, a screw 69 made of an electrical conductor is arranged so as to penetrate the lower casing 62 of the arm segment 38c, and is secured to a hub 30a of one of the current-supplying electrodes 30 having a hollow structure. The current-supply circuit 42 in FIG. 5 is connected with the screw 69 via a wire (not shown).

An opening 66 is formed at an end of each of the arm segments 38a, 38b, and 38c, whereas a pair of protrusions 68 are formed at the other end of each of the arm segments 38a, 38b, and 38c (see also FIG. 4). An opening 76 is formed at each end of the handle segment 34. The protrusions 68 of the arm segment 38a are inserted into one of the openings 76 of the handle segment 34, and are rotatably jointed by pins 80 to inner walls 82 formed at the handle segment 34. Thus, the arm segment 38a is rotatable about coaxial pins 80 within the handle segment 34. The protrusions 68 of the arm segment 38b are inserted into the opening 66 of the arm segment 38a, and are rotatably jointed by pins 80 to inner walls 84 formed at the arm segment 38a. Thus, the arm segment 38b is rotatable about coaxial pins 80 within the arm segment 38a. The protrusions 68 of the arm segment 38c are inserted into the opening 66 of the arm segment 38b, and are rotatably jointed by pins 80 to inner walls 84 formed at the arm segment 38b. Thus, the arm segment 38c is rotatable about coaxial pins 80 within the arm segment 38b. The opening 66 of the arm segment 38c is blocked with a blockage plate 86.

Thus, in the electrode supporting member 33, neighboring segments are connected rotatably with each other. The electrode supporting member 33 further includes rotation-angle restricting parts for restricting relative rotation-angles between neighboring segments. More specifically, the lower casing 72 of the handle segment 34 includes a lateral rotation-angle restricting wall 90 and a lower rotation-angle restricting wall 92 that are located in the vicinity of the opening 76 of the handle segment 34. The rotation of the arm segment 38a relative to the handle segment 34 is restricted by the lateral rotation-angle restricting wall 90 and the lower rotation-angle restricting wall 92. More specifically, rotation in the clockwise direction of the arm segment 38a relative to the handle segment 34 in FIG. 6 is stopped when the side edges of the protrusions 68 of the arm segment 38a strike against the lateral rotation-angle restricting wall 90, whereas rotation in the counterclockwise direction of the arm segment 38 is stopped when the lower edges of the protrusions 68 of the arm segment 38a strike against the lower rotation-angle restricting wall 92. Therefore, the angular difference between the angle of the bottom-right corner (in FIG. 6) of the protrusions 68 of the arm segment 38a and the angle formed by the meeting of the lateral rotation-angle restricting wall 90 and the lower rotation-angle restricting wall 92 of the handle segment 34 is the permissible range of rotation of the arm segment 38a relative to the handle segment 34. The permissible rotational angular range is indicated by θ1 in FIG. 7.

In addition, the lower casing 62 of each of the arm segments 38a and 38b includes a lateral rotation-angle restricting wall 94 and a lower rotation-angle restricting wall 96 as rotation-angle restricting parts that are located in the vicinity of the opening 66 thereof. Rotation in the clockwise direction of the arm segment 38b relative to the arm segment 38a in FIG. 6 is stopped when the side edges of the protrusions 68 of the arm segment 38b strike against the lateral rotation-angle restricting wall 94 of the arm segment 38a, whereas rotation in the counterclockwise direction of the arm segment 38b is stopped when the lower edges of the protrusions 68 of the arm segment 38b strike against the lower rotation-angle restricting wall 96 of the arm segment 38a. Therefore, the angular difference between the angle of the bottom-right corner (in FIG. 6) of the protrusions 68 of the arm segment 38b and the angle formed by the meeting of the lateral rotation-angle restricting wall 94 and the lower rotation-angle restricting wall 96 of the arm segment 38a is the permissible range of rotation of the arm segment 38b relative to the arm segment 38a. The permissible rotational angular range is indicated by θ2 in FIG. 7.

Rotation in the clockwise direction of the arm segment 38c relative to the arm segment 38b in FIG. 6 is stopped when the side edges of the protrusions 68 of the arm segment 38c strike against the lateral rotation-angle restricting wall 94 of the arm segment 38b, whereas rotation in the counterclockwise direction of the arm segment 38c is stopped when the lower edges of the protrusions 68 of the arm segment 38c strike against the lower rotation-angle restricting wall 96 of the arm segment 38b. Therefore, the angular difference between the angle of the bottom-right corner (in FIG. 6) of the protrusions 68 of the arm segment 38c and the angle formed by the meeting of the lateral rotation-angle restricting wall 94 and the lower rotation-angle restricting wall 96 of the arm segment 38b is the permissible range of rotation of the arm segment 38c relative to the arm segment 38b. The permissible rotational angular range is indicated by θ3 in FIG. 7.

Figure 7:
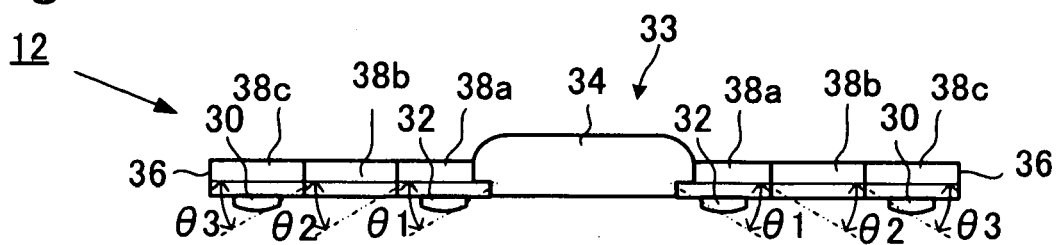
FIG. 7 is a front view showing the impedance-measuring unit 12 and showing a permissible range of each relative rotation-angle between neighboring segments in the electrode supporting member.

FIG. 7 is a front view showing the impedance measuring unit 12 and showing a permissible range of each relative rotation-angle between neighboring segments in the electrode supporting member 33. In the state shown in FIG. 7, all segments are straightly elongated, and all of the relative rotation-angles between segments are zero. In this state, the side edges of the protrusions 68 (shown in FIG. 6) of the arm segment 38a are in contact with the lateral rotation-angle restricting wall 90, the side edges of the protrusions 68 of the arm segment 38b are in contact with the lateral rotation-angle restricting wall 94 of the arm segment 38a, and the side edges of the protrusions 68 of the arm segment 38c are in contact with the lateral rotation-angle restricting wall 94 of the arm segment 38b.

From the state in FIG. 7, the arm segment 38a can be rotated relative to the handle segment 34 by the permissible rotational angular range θ1 to the inclined position indicated by the phantom line. When the arm segment 38a is rotated to the inclined position indicated by the phantom line, the lower edges of the protrusions 68 of the arm segment 38a (shown in FIG. 6) are brought into contact with the lower rotation-angle restricting wall 92.

From the state in FIG. 7, the arm segment 38b can be rotated relative to the arm segment 38a by the permissible rotational angular range θ2 to the inclined position indicated by the phantom line. When the arm segment 38b is rotated to the inclined position indicated by the phantom line, the lower edges of the protrusions 68 of the arm segment 38b (shown in FIG. 6) are brought into contact with the lower rotation-angle restricting wall 96 of the arm segment 38a.

From the state in FIG. 7, the arm segment 38c can be rotated relative to the arm segment 38b by the permissible rotational angular range θ3 to the inclined position indicated by the phantom line. When the arm segment 38c is rotated to the inclined position indicated by the phantom line, the lower edges of the protrusions 68 of the arm segment 38c (shown in FIG. 6) are brought into contact with the lower rotation-angle restricting wall 96 of the arm segment 38b.

With such a structure, since the electrode supporting member 33 includes segments (the handle segment 34 and the arm segments 38a, 38b, and 38c) connected mutually rotatably, and since the plurality of electrodes 30 and 32 are respectively mounted on different segments, by simply positioning the electrode supporting member 33 as shown in FIG. 3, the electrode supporting member 33 can be bent at the edges of segments around the outline of the abdomen of a human subject 14 due to gravitational force exerted on the individual elements of the electrode supporting member 33, so that the electrodes 30 and 32 protruding from the electrode supporting member 33 are brought into contact with the abdomen of the human subject 14. Thus, the electrodes 30 and 32 can be easily arranged at abdomens of human subjects 14. In addition, since the electrode supporting member 33 can be bent and be made to conform to the outline of the abdomen of a human subject 14 by the gravitational force exerted on the individual elements of the electrode supporting member 33, whereby the electrodes 30 and 32 are brought into contact with the abdomen of the human subject 14, no other force is necessary for maintaining the electrodes 30 and 32 in contact with the abdomen of the human subject 14. Thus, with respect to a single subject 14, each of the electrodes 30 and 32 comes into contact with the abdomen at a substantially constant force and at a substantially constant orientation (i.e., with a high level of reproducibility).

Figure 8:
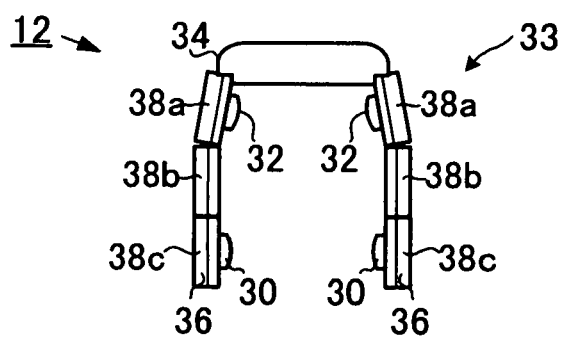
FIG. 8 is a front view showing the impedance measuring unit in which a handle segment is held by an operator if the rotation-angle restricting parts of the present invention are not provided.

Furthermore, the rotation-angle restricting parts prevent mutual overrotation of segments. Since the cross section of the abdomen of a human subject 14 is generally oval, it is preferable that the electrode supporting member 33 be arranged around the abdomen of the human subject 14 in such a manner that the electrode supporting member 33 is bent at an obtuse angle, rather than at an acute angle, at the edges of the segments, so that each segment is arranged substantially parallel to a part of the generally oval outline. Once the electrode supporting member 33 is bent at a small angle, e.g., an acute angle, by mutual overrotation of segments, it takes some time to suitably arrange the electrode supporting member 33 around the abdomen of the human subject. FIG. 8 is a front view showing the impedance measuring unit 12 of which a handle segment 34 is held by an operator if the rotation-angle restricting parts are not provided. In the state shown in FIG. 8, each arm segment 38a is rotated relative to the handle segment 34 by an angle near the proper angle since there are no rotation-angle restricting parts. Accordingly, the electrode supporting member 33 cannot be promptly transformed into a state (e.g., shown in FIG. 3) which conforms to the outline the abdomen of the human subject 14. By virtue of preventing mutual overrotation of segments with the rotation-angle restricting parts, the time for suitably arranging the impedance measuring unit 12 around the abdomen of the human subject can be saved.

In each arm 36, at least one (specifically, one in this embodiment) segment 38b is interposed between the segment 38c on which one of the current-supplying electrodes 30 is mounted and the segment 38a on which one of the voltage-measurement electrodes 32 is mounted. Therefore, the degree of freedom of movement of the mechanism can be enhanced and the length of the segments 38a and 38c on which electrodes 30 and 32 are mounted can be shortened, in comparison with a design in which the segment 38c on which the current-supplying electrode 30 is mounted is directly joined with the segment 38a on which the voltage-measurement electrode 32 is mounted. Thus, with respect to a plurality of human subjects 14 of different body types, the electrode supporting member 33 can be bent and conform to the various outlines of the abdomen, and with respect to a particular human subject 14, each of the electrodes 30 and 32 may be brought into contact with the abdomen at a substantially constant orientation.

Preferably, the rotation-angle restricting parts in the electrode supporting member 33 are provided such that the farther from the central handle segment 34, the less the permissible rotational angular range of the relative rotation of neighboring segments. Consequently, it is preferable that $\theta 1 > \theta 2 > \theta 3$. For a common human body type, such restrictions of rotation-angles are preferable than a design in which $\theta 1 < \theta 2 < \theta 3$ because such restrictions of rotation-angles facilitate the transformation of the electrode supporting member 33 into a bent shape conforming to the usual outline of the abdomen of a human subject, and the electrodes 30 and 32 are arranged at appropriate positions with high reproducibility. Furthermore, the electrode supporting member 33 can be promptly transformed from a straightly elongated condition into a bent shape conforming to the outline of the abdomen of a human subject.

As shown in FIG. 6, each of the electrodes 30 and 32 includes a convex curved surface 100 brought into contact with the abdomen of the human subject 14 and a cylindrical outer peripheral surface 102 smoothly continuing from the convex curved surface 100. The length of the outer peripheral surface 102 along the axial direction of the electrode is preferably equal to or greater than 3.5 millimeters, and is more preferably equal to or greater than 5.0 millimeters. It is preferable to determine the length of the outer peripheral surface 102 sufficiently so that the convex curved surface is arranged apart from the electrode supporting member 33.

Figure 9:
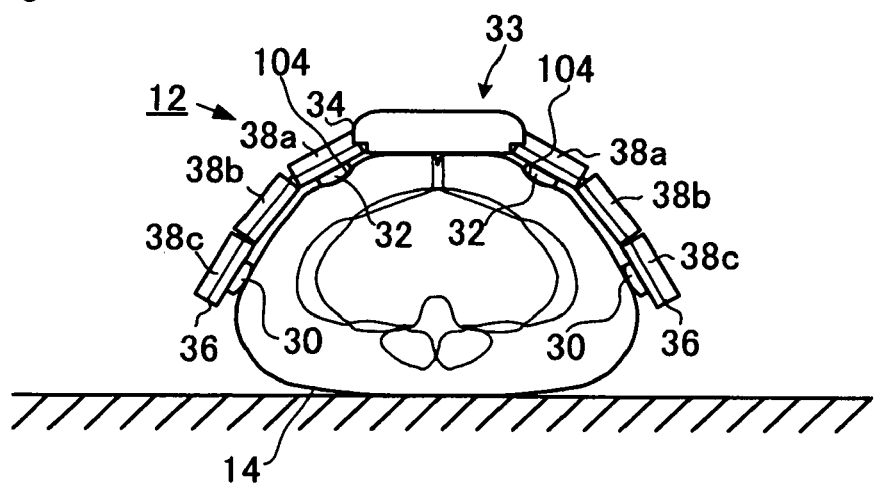
FIG. 9 is a front view showing the impedance measuring unit when placed on a human subject with steep undulations on the anterior surface thereof due to the abdominal muscle.

As shown in FIG. 9, a human subject 14 with a well-developed abdominal muscle, or a thin human subject 14, may have steeper undulations on the anterior surface thereof due to the abdominal muscle than those of the human subject 14 shown in FIG. 3. Therefore, if the electrodes 30 and 32 do not include convex curved surfaces, there is a possibility that electrodes 30 and 32 will not come into contact with the skin of the human subject 14 even if the electrodes 30 and 32 are faced toward the indentations 104 of the abdominal muscle (positioned inside the indentations 104 of the abdominal muscle). In contrast, when each of the electrodes 30 and 32 includes a convex curved surface 100 brought into contact with the abdomen of the human subject 14 and the convex curved surfaces 100 are arranged apart from the electrode supporting member 33 as in this embodiment, the electrodes 30 and 32 securely come into contact with the skin of the human subject 14 even if the electrodes 30 and 32 are faced toward the indentations 104 of the abdominal muscle (i.e., are positioned inside the indentations 104 of the abdominal muscle).

Modifications

In the above-described embodiment, the rotation-angle restricting parts are walls (the lateral rotation-angle restricting wall 90 or 94 and the lower rotation-angle restricting wall 92 or 96) located within segments neighboring the segments of which the rotation is restricted. However, it is not intended to limit the scope of the present invention to the embodiment. Rotation-angle restricting parts may be pins, rods, steps, or any other means for restricting rotation-angles fixed or formed at neighboring segments.

In the above-described embodiment, plural sensors 22 are fixed to the frame 16. However, it is possible for a sensor to be attached movably to each of the legs 18 and 18b, and for each sensor to be driven at known positions for measuring distances from the corresponding sensor to a plurality of measured points on the outline of the human subject.

In the above-described embodiment, optical distance sensors 22 are used as distance measuring devices for measuring distances from a plurality of known positions to a plurality of measured points on the outline of the human subject 14 in a noncontact manner. However, distance measuring devices may be other types of noncontact distance measuring devices.

In the above-described embodiment, body composition indexes are calculated directly from the abdominal width and the bioimpedance of the human subject 14. However, it is possible for another index (for example, the cross-sectional area of the abdomen or the waist circumference) to be calculated from the abdominal width, and then for the body composition indexes to be calculated from such an index and the bioimpedance.

In the above-described embodiment, for determining the abdominal width, the sensors 22a through 22h are deployed in the transverse plane that passes through the navel of the human subject 14 and is vertical to the median line of the human subject 14. However, by adjusting the location of the light emitter 26 relative to the sensors 22a through 22h, the sensors 22a through 22h may be deployed in another transverse plane vertical to the median line of the human subject 14 for determining the abdominal width.

In the above-described embodiment, for measuring the bioimpedance of the abdomen, the electrodes 30 and 32 may also be deployed in the transverse plane that passes through the navel of the human subject 14 and is vertical to the median line of the human subject 14. However, by adjusting at least one of the location of the mark and the location of the light receiving elements on the handle 34 relative to the electrodes 30 and 32, the electrodes 30 and 32 may be deployed in another transverse plane vertical to the median line of the human subject 14 for measuring the bioimpedance of the abdomen.

What is claimed is:

1. An abdominal impedance measurement apparatus comprising:
    a plurality of electrodes for measuring an abdominal impedance of a human subject; and
    an electrode supporting member for supporting the electrodes in such a manner that the electrodes protrude from the electrode supporting member, the electrode supporting member comprising a plurality of segments aligned in a direction, each single electrode being mounted on a segment that is different from every other segment on which another electrode is mounted, such that no two electrodes are mounted on the same segment, neighboring segments being connected rotatably with each other, the electrode supporting member comprising rotation-angle restricting parts for restricting relative rotation-angles between neighboring segments,
    wherein the plurality of electrodes comprise two current-supplying electrodes adapted to contact an abdomen of the human subject for applying an electrical current to the abdomen of the human subject and two voltage-measurement electrodes adapted to be brought into contact with two parts of the abdomen of the human subject for measuring a voltage between the parts with which the voltage-measurement electrodes are in contact, the current-supplying electrodes being mounted on two of the segments of the electrode supporting member, the voltage-measurement electrodes being mounted on two of the segments of the electrode supporting member that are different from the segments on which the current-supplying electrodes are mounted,
    wherein at least one segment on which no electrode is mounted exists between the segment on which one of the current-supplying electrodes is mounted and the segment on which one of the voltage-measurement electrodes is mounted, and
    wherein the rotation-angle restricting parts of the electrode supporting member are provided such that the rotation-angle restricting parts located nearer a center of the electrode supporting member restrict a relative rotation-angle between neighboring segments within a larger range and such that the rotation-angle restricting parts located farther from the center of the electrode supporting member restrict a relative rotation-angle between neighboring segments within a smaller range.

2. The abdominal impedance measurement apparatus of claim 1, wherein segments each on which no electrode is mounted exist at all positions between neighboring segments on which the electrodes are mounted.

3. The abdominal impedance measurement apparatus of claim 1, wherein neighboring segments are rotatably jointed by pins, and the rotation-angle restricting parts are adapted to restrict relative rotation-angles about the pins between neighboring segments.

4. The abdominal impedance measurement apparatus of claim 1, wherein each of the electrodes comprises a cylindrical part protruding from the electrode supporting member and a convex curved surface adapted to be brought into contact with the abdomen of the human subject, the convex curved surface being arranged at a distal end of the cylindrical part opposite to the electrode supporting member and apart from the electrode supporting member.

5. The abdominal impedance measurement apparatus of claim 1, wherein the electrode supporting member is adapted to be placed on the abdomen of the human subject lying supine in such a manner that the center of the electrode supporting member is adapted to be positioned on the center of abdomen of the human subject, and the electrode supporting member is bent due to gravitational force.

6. The abdominal impedance measurement apparatus of claim 4, wherein the electrode supporting member is adapted to be placed on the abdomen of the human subject lying supine and is bent due to gravitational force.

7. An abdominal impedance measurement apparatus comprising:
    a plurality of electrodes for measuring an abdominal impedance of a human subject; and
    an electrode supporting member for supporting the electrodes in such a manner that the electrodes protrude from the electrode supporting member, the electrode supporting member comprising a plurality of segments aligned in a direction, each single electrode being mounted on a segment that is different from every other segment on which another electrode is mounted, such that no two electrodes are mounted on the same segment, neighboring segments being connected rotatably with each other, the electrode supporting member comprising rotation-angle restricting parts for restricting relative rotation-angles between neighboring segments,
    wherein the plurality of electrodes comprise two current-supplying electrodes adapted to contact an abdomen of the human subject for applying an electrical current to the abdomen of the human subject and two voltage-measurement electrodes adapted to be brought into contact with two parts of the abdomen of the human subject for measuring a voltage between the parts with which the voltage-measurement electrodes are in contact, the current-supplying electrodes being mounted on two of the segments of the electrode supporting member, the voltage-measurement electrodes being mounted on two of the segments of the electrode supporting member that are different from the segments on which the current-supplying electrodes are mounted, wherein at least one segment on which no electrode is mounted exists between the segment on which one of the current-supplying electrodes is mounted and the segment on which one of the voltage-measurement electrodes is mounted, and wherein each of the rotation-angle restricting parts comprises first walls of one of the segments corresponding to the rotation-angle restricting part and second walls of the other of the segments corresponding to the rotation-angle restricting part, the first walls being capable of being brought into contact with the second walls, whereby the first and the second walls define the range of the relative rotation-angle between the neighboring segments.

8. The abdominal impedance measurement apparatus of claim 7, wherein one of two neighboring segments comprises an opening and the other of the two neighboring segments comprises a protrusion inserted into the opening, the protrusion having a corner defined by the first walls, the second walls being located within the segment having the opening, the second walls being spaced apart at an angular interval in which the corner of the protrusion defined by the first walls is located, whereby the first and the second walls define the range of the relative rotation-angle between the two neighboring segments.

* * * * *